US012329137B2

(12) United States Patent
Sohn

(10) Patent No.: US 12,329,137 B2
(45) Date of Patent: Jun. 17, 2025

(54) METHOD OF PREPARING MOUSE MODEL OF HERPES

(71) Applicant: AJOU UNIVERSITY INDUSTRY-ACADEMIC COOPERATION FOUNDATION, Suwon-si (KR)

(72) Inventor: Seonghyang Sohn, Suwon (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 794 days.

(21) Appl. No.: 17/622,364

(22) PCT Filed: Jun. 25, 2020

(86) PCT No.: PCT/KR2020/008248
§ 371 (c)(1),
(2) Date: Dec. 23, 2021

(87) PCT Pub. No.: WO2020/262972
PCT Pub. Date: Dec. 30, 2020

(65) Prior Publication Data
US 2022/0232811 A1 Jul. 28, 2022

(30) Foreign Application Priority Data
Jun. 25, 2019 (KR) .................. 10-2019-0075872

(51) Int. Cl.
*A01K 67/027* (2024.01)
(52) U.S. Cl.
CPC ........ *A01K 67/027* (2013.01); *A01K 2207/20* (2013.01); *A01K 2227/105* (2013.01); *A01K 2267/03* (2013.01)
(58) Field of Classification Search
CPC .............. A01K 67/027; A01K 2207/20; A01K 2227/105; A01K 2267/03; A01K 2207/30; A01K 2267/0337; A01K 2207/00; C12N 2710/16631; G01N 33/5023; G01N 2333/03; G01N 2333/035
See application file for complete search history.

(56) References Cited

U.S. PATENT DOCUMENTS 6,337,324 B1 * 1/2002 Harmenburg et al. .................. A61K 31/56
2017/0281751 A1 10/2017 Allen

FOREIGN PATENT DOCUMENTS

| CN | 109330732 A | * | 11/2018 | ........... A61K 39/245 |
|----|-------------|---|---------|------------------------|
| CN | 109769748 A |   | 5/2019  |                        |
| RU | 0002709842  | * | 12/2018 | ............. G09B 23/28 |
| WO | 2010/014241 A2 |   | 2/2010  |                     |

OTHER PUBLICATIONS

Dufour et al., "The Ribonucleotide Reductase R1 Subunits of Herpes Simplex Virus 1 and 2 Protect Cells against Poly(I C)-Induced Apoptosis", Journal of Virology, Sep. 2011, p. 8689-8701 (Year: 2011).*
Mott et al., "Macrophage IL-12p70 Signaling Prevents HSV-1 Induced CNS Autoimmunity Triggered by Autoaggressive CD4+ Tregs", Investigative Ophthalmology & Visual Science, (2011), 52(5), p. 2321-2332 (Year: 2011).*
Ponce de Leon et al., "Ribonucleotide Reductase from Herpes Simplex Virus (Types 1 and 2) Infected and Uninfected KB Cells: Properties of the Partially Purified Enzymes", J. gen. Virol., Feb. 1977, p. 163-173 (Year: 1977).*
Yang et al., "T cell derived lymphotoxin limits TH1 response during HSV-1 infection", Scientific Reports (2018)8:17727 (Year: 2018).*
Furlong et al., "The Large Subunit of Herpes Simplex Virus Type 1 Ribonucleotide Reductase: Expression in *Escherichia coli* and Purification", Virology 182 (1991), p. 846-851 (Year: 1991).*
AR Awan et al., "Combinations of antiviral and anti-inflammatory preparations for the topical treatment of herpes simplex virus assessed using a murine zosteriform infection model", Antiviral Chemistry & Chemotherapy, 1998, vol. 9, No. 1, pp. 19-24 (6 pages total).
D.V. Datta et al., "Effect of corticosteroids on mouse hepatitis virus infection", Gut, 1969, vol. 10, No. 7, pp. 522-529 (8 pages total).
A.K.M.M. Anower, et al., "The role of classical and alternative macrophages in the immunopathogenesis of herpes simplex virus-induced inflammation in a mouse model", Journal of Dermatological Science, 2014, vol. 73, pp. 198-208 (12 pages total).
Clayton E. Wheeler et al., "The Effect of Hydrocortisone on the Production of Herpes Simplex Virus in Tissue Culture", The Journal of Investigative Dermatology, 1961, pp. 89-97 (10 pages total).
Joseph M. Blondeau et al., "Herpes Simplex Virus Infections in Male and Female Mice Following Pinna Inoculation: Reponses to Primary Infection and Artificially Induced Recurrent Disease", Journal of Medical Virology, 1989, vol. 29, pp. 320-326 (8 pages total).
Christopher M. Hull et al., "Novel Composite Efficacy Measure to Demonstrate the Rationale and Efficacy of Combination Antiviral-Anti-Inflammatory Treatment for Recurrent Herpes Simplex Labialis", Antimicrobial Agents and Chemotherapy, Mar. 2014, vol. 58, No. 3, pp. 1273-1278 (6 pages total).

(Continued)

*Primary Examiner* — Valerie E Bertoglio
(74) *Attorney, Agent, or Firm* — Sughrue Mion, PLLC

(57) ABSTRACT

A method of preparing a mouse model of herpes using a herpes simplex virus and hydrocortisone, and a mouse model of herpes prepared using the method are disclosed. The method makes it possible to obtain an animal model in which symptoms of herpes clearly appear. The obtained animal model can be widely used in the development of therapeutic agents for herpes simplex virus infection. A use of the mouse model in screening and developing a candidate therapeutic agent is also disclosed.

5 Claims, 6 Drawing Sheets
Specification includes a Sequence Listing.

(56) References Cited

OTHER PUBLICATIONS

Brent A. Stanfield et al., "Intramuscular vaccination of guinea pigs with the live-attenuated human herpes simplex vaccine VC2 stimulates a transcriptional profile of vaginal Th17 and regulatory Tr1 responses" Vaccine, 2018, vol. 36, pp. 2842-2849 (8 pages total).

Masahiko Kurokawa et al., "Antiviral traditional medicines against herpes simplex virus (HSV-1), poliovirus, and measles virus in vitro and their therapeutic efficacies for HSV-1 infection in mice", Antiviral Research, 1993, vol. 22, pp. 175-188 (14 pages total).

Taksina Chuanasa et al., "Anti-herpes simplex virus (HSV-1) activity of oxyresveratrol derived from Thai medicinal plant: Mechanism of action and therapeutic efficacy on cutaneous HSV-1 infection in mice", Antiviral Research, 2008, vol. 80, pp. 62-70 (9 pages total).

\* cited by examiner

US 12,329,137 B2

METHOD OF PREPARING MOUSE MODEL OF HERPES

CROSS REFERENCE TO RELATED APPLICATIONS

This application is a National Stage of International Application No. PCT/KR2020/008248 filed Jun. 25, 2020, claiming priority based on Korean Patent Application No. 10-2019-0075872 filed Jun. 25, 2019.

SEQUENCE LISTING

The content of the electronically submitted sequence listing, file name: Sequence_Listing_As_Filed.txt; size: 1,835 bytes; and date of creation: Dec. 22, 2021, filed herewith, is incorporated herein by reference in its entirety.

TECHNICAL FIELD

The present invention relates to a method of preparing a mouse model of herpes. More particularly, the present invention relates to a method of preparing a mouse model of herpes using a herpes simplex virus and hydrocortisone, and a mouse model of herpes prepared by way of the method.

BACKGROUND ART

According to a report of the World Health Organization, as of 2015, 3.7 billion of the world's population under the age of 50, or 67% of the total population, are infected with herpes simplex virus type 1 (HSV-1). It is estimated that more than 100 million people worldwide are infected with herpes simplex virus type 1 every year. In particular, it has been reported that oral or labial infection makes up 80% or more of the infections with herpes simplex virus type 1. During herpes simplex virus infection, herpes simplex virus may be spread by contact with the mucous membrane of skin even in the latent period during which symptoms do not appear. Herpes simplex virus may be reactivated after infecting the ganglion. Latency and reactivation are repeated throughout life depending on the patient's immune status. In particular, herpes simplex virus may cause fatal complications in the infected person when the level of immunity is lowered. It is known that a mother who is infected with herpes simplex virus in her genitals may transmit herpes simplex virus to her newborn baby through childbirth, and newborns infected with herpes simplex virus in the early stages of childbirth are more likely to suffer nerve and brain damage. In general, when infected with herpes simplex virus, it is known that the symptoms of infection appear for 15 to 23 days from the time of initial infection, and the symptoms of infection appear for 9 to 11 days at the time of relapse. Accordingly, studies are being actively conducted to develop a vaccine against herpes simplex virus, but significant results have thus far not been reported.

Another research direction for the treatment of herpes simplex virus infection is the development of an animal model showing the symptoms of infection in order to develop a vaccine against herpes simplex virus type 1. For example, WO 2010/014241 discloses a method of preparing an equine model of herpesviral neuropathy by exposing the equine model to a herpes simplex virus-specific CTL precursor at a low level and then inoculating the equine model with a neuropathogenic herpes simplex virus. However, the animal model prepared by such a method is not used as an animal model since herpes lesions appearing around the lips are unclear.

DISCLOSURE

Technical Problem

As a result of intensive research efforts by the present inventors to develop an animal model in which herpes lesions clearly appear around the lips of the animal, it has been confirmed that an animal model in which herpes lesions clearly appear around the lips of the animal can be prepared when herpes simplex virus and hydrocortisone are used, thereby completing the present invention.

Technical Solution

The main object of the present invention is to provide a method of preparing a mouse model of herpes using a herpes simplex virus and hydrocortisone.

Another object of the present invention is to provide a mouse model of herpes prepared by way of the method.

Still another object of the present invention is to provide use of the mouse model of herpes for the development of therapeutic agents for herpes.

Advantageous Effects

When the preparation method provided in the present invention is used, an animal model in which the symptoms of herpes clearly appear can be prepared, and thus the animal model can be widely used in the development of therapeutic agents for herpes simplex virus infection.

BEST MODE

Figure 1:
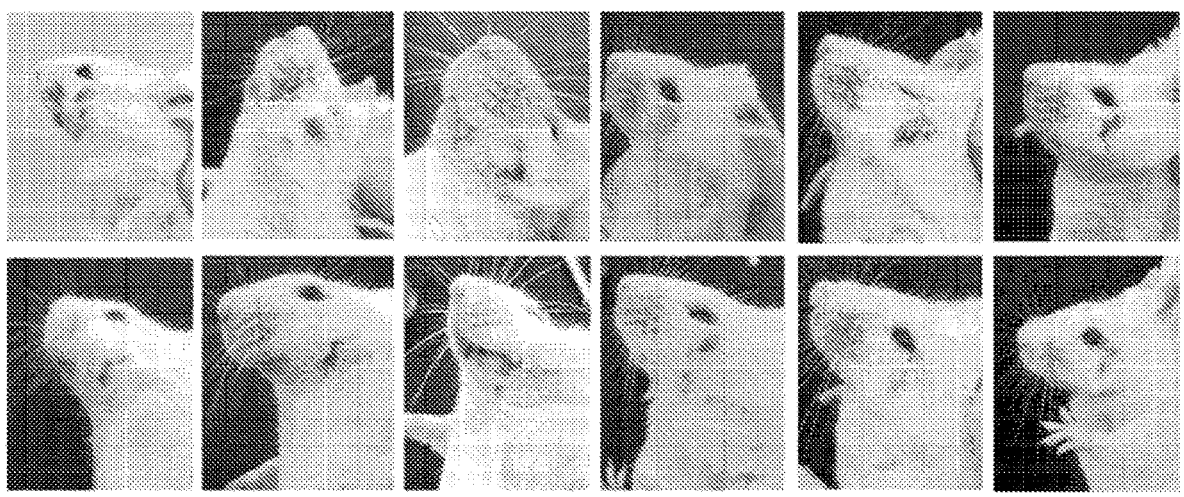
FIG. 1 is photographs of blistered facial parts of mouse models of herpes prepared using twelve 5-week-old ICR mice.

An aspect of the present invention for achieving the objects provides a method of preparing a mouse model of herpes, which includes (a) damaging skin of a mouse, inoculating the damaged site with herpes simplex virus type 1 (HSV-1), and then rearing the mouse; and (b) injecting the reared mouse with hydrocortisone, and a mouse model of herpes prepared by way of the method.

In the present invention, the mouse used may be an ICR mouse as an example, and may be an ICR mouse bred and reared in SPF (specific-pathogen-free) conditions as another example, but is not particularly limited thereto.

The site inoculated with herpes simplex virus type 1 may be the skin region of a mouse as an example, and may be the skin region of the pinna of a mouse as another example, but is not particularly limited thereto.

The amount of herpes simplex virus type 1 inoculated may be $1 \times 10^3$ pfu to $1 \times 10^5$ pfu as an example, may be $1 \times 10^4$ pfu to $5 \times 10^4$ pfu as another example, and may be $2 \times 10^4$ pfu as still another example, but is also not particularly limited thereto.

The inoculation with herpes simplex virus type 1 may be performed one or more times. In the case of multiple inoculation, the inoculation may be repeatedly performed by performing the next inoculation when 5 to 15 days elapse after the previous inoculation has been performed.

The injection method of hydrocortisone may be performed by way of methods such as intramuscular injection, intraperitoneal injection, and vascular injection as an example, and may be performed by way of an intraperitoneal injection method as another example, but is not particularly limited thereto.

The hydrocortisone injection may be performed from the day after the inoculation with herpes simplex virus type 1 has been performed.

As an aspect, when the inoculation with herpes simplex virus type 1 is performed only one time, hydrocortisone may be injected every day for 3 to 15 days from the day after the inoculation has been performed as an example, hydrocortisone may be injected every day for 3 to 10 days from the day after the inoculation has been performed as another example, hydrocortisone may be injected every day for 3 to 5 days from the day after the inoculation has been performed as still another example.

As another aspect, when the inoculation with herpes simplex virus type 1 is repeatedly performed, hydrocortisone may be injected every day during the time between the previous inoculation and the next inoculation, and hydrocortisone may be injected every day for 3 to 15 days from the day after the last inoculation has been completed, hydrocortisone may be injected every day for 3 to 10 days from the day after the last inoculation has been completed, or hydrocortisone may be injected every day for 3 to 5 days from the day after the last inoculation has been completed.

The amount of hydrocortisone injected may be 10 μg/day to 1000 μg/day per average body weight of mice (25 g) as an example, may be 150 μg/day to 500 μg/day per average body weight of mice (25 g) as another example, and may be 150 μg/day to 200 μg/day per average body weight of mice (25 g) as still another example, but is not particularly limited thereto.

Another aspect of the present invention provides a mouse model of herpes prepared by way of the method described above.

According to an embodiment, in the mouse model of herpes, blisters, known as one of the major symptoms of herpes simplex virus infection, are observed on the face of the mouse, especially around the lips, and it is possible to easily confirm whether herpes simplex virus infection has occurred, whether herpes simplex virus infection is treated or not, and the like through the observation of blisters.

According to another embodiment, the expression level of HSV ribonucleotide reductase, which is involved in the proliferation of HSV-1, increases in immune-related tissues such as lymph node and spleen of the mouse model of herpes as compared to that of a normal mouse.

According to still another embodiment, the expression level of immunoregulatory genes in immune-related tissues such as lymph node and spleen of the mouse model of herpes is significantly different from that of a normal mouse.

As an example, the expression level of T-bet gene, which is a master regulator of T helper type 1 (Th1) cells, increases in the mouse model of herpes as compared to that in a normal mouse. This has been analyzed to rapidly increase the level of Th1 and increase the level of IFN-γ secreted from Th1 so that the infected HSV-1 can be promptly removed.

As another example, the expression level of FoxP3 gene, which is a master regulator of regulatory T cells (Treg), decreases, and the expression level of FoxP3 gene after the administration of therapeutic agent increases in the mouse model of herpes as compared to those in a normal mouse. This is because regulatory T cells have a role in suppressing the activity of proinflammatory immune cells, and it has been analyzed that the expression level of FoxP3 gene increases when a therapeutic agent is administered to the mouse model of herpes, and inflammation removal efficiently proceeds.

Meanwhile, such changes in the expression level of immunoregulatory genes are basically due to HSV-1 infection, but it has been analyzed that such changes are significantly affected by hydrocortisone, which amplifies the level of HSV-1 infection.

In fact, it has been confirmed that mice administered with HSV-1 and hydrocortisone in combination have a relatively higher synchronization rate with actual infected mice than mice administered with HSV singly in the preparation of mouse models of herpes provided in the present invention. In addition, it has been confirmed that the synchronization rate of mouse models of herpes prepared by administering HSV-1 and hydrocortisone in combination with actual infected mice increases in proportion to the dose of hydrocortisone.

Another aspect of the present invention provides use of the mouse model of herpes for the development of a therapeutic agent for herpes.

As described above, it has been confirmed that the mouse model of herpes provided in the present invention has a significantly increased synchronization rate with mice infected with herpes simplex virus compared to conventional model animals of herpes, and thus it is possible to more effectively develop a therapeutic agent for herpes simplex virus infection when the mouse model of herpes provided in the present invention is used.

DETAILED DESCRIPTION

Hereinafter, the present invention will be described in more detail with reference to Examples. However, these Examples are for illustrative purposes only, and the scope of the present invention is not limited to these Examples.

Example 1: Construction of Mouse Model of Herpes

The ear inner conch of a large number of 5-week-old ICR mice bred and reared in SPF (specific pathogen free) conditions was injured by being scratched with an injection needle at a strength sufficient to prevent blood from bleeding out, then the injured site was first inoculated with 20 μL of HSV-1 (herpes simplex virus type 1, F strain) solution ($1×10^6$ pfu/mL), and the mice were reared for 10 days. Next, the same injured site was secondarily inoculated with the same dose of HSV-1. One time a day for 5 days from the day after the first inoculation had been performed and one time a day for 5 days from the day after the second inoculation had been performed, hydrocortisone was intraperitoneally injected into each mouse at 50 μg/day to 500 μg/day. Thereafter, the faces of the mice were observed, mice having blisters formed around the lips were selected, and these were used as mouse models of herpes (FIG. 1).

FIG. 1 is photographs of blistered facial parts of mouse models of herpes prepared using twelve 5-week-old ICR mice.

Example 2: Validation of Mouse Model of Herpes

In order to confirm whether the mouse models of herpes prepared in Example 1 could be used as an animal model reflecting the symptoms of herpes, the changes according to the treatment of the mouse models with a medicine for external application to treat herpes were analyzed.

Figure 2:
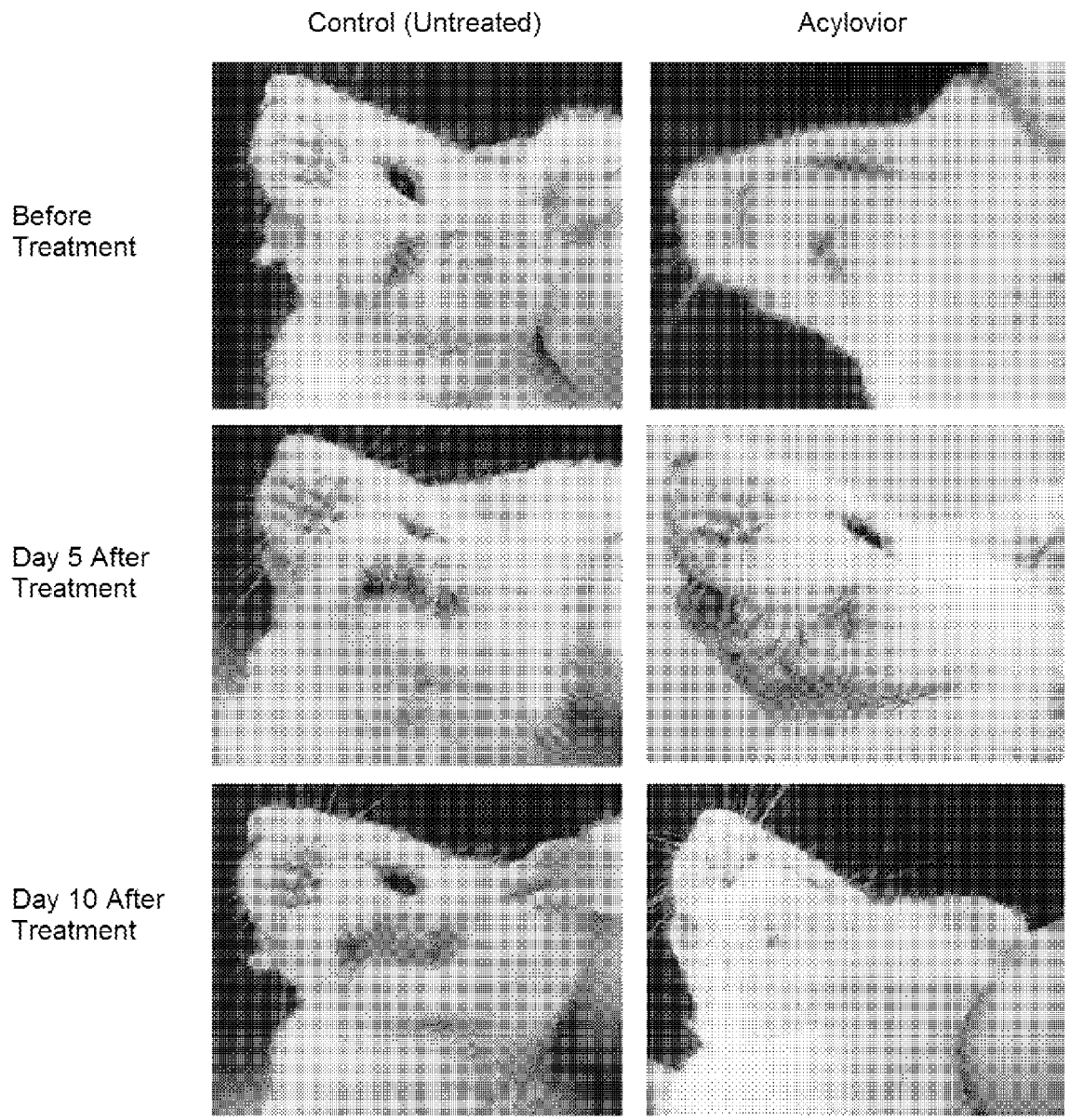
FIG. 2 is photographs illustrating the results acquired by applying Acyclovir ointment to the lesion site of mouse models of herpes for 10 days and then comparing the changes in the skin lesions.

Example 2-1: Treatment with Medicine for External Application to Treat Herpes To the skin lesion site of the mouse models of herpes prepared in Example 1, 1 mg of Acyclovir ointment, known as a remedy for herpes, was applied one time a day for 10 days, and the changes in the skin lesions were compared (FIG. 2). In this case, mouse models of herpes not treated with Acyclovir ointment were used as a control group.

FIG. 2 is photographs illustrating the results acquired by applying Acyclovir ointment to the lesion site of mouse models of herpes for 10 days and then comparing the changes in the skin lesions.

As can be seen from FIG. 2, it has been confirmed that there is no change in the skin lesion site as time elapses in the case of the control group, but the size of the lesion site decreases and the symptoms are improved as the application time elapses in the case of applying Acyclovir ointment to the lesion sites of mouse models of herpes.

Example 2-2: Analysis of Expression Level of HSV Ribonucleotide Reductase

As is known, HSV ribonucleotide reductase is involved in the proliferation of HSV-1, and thus changes in the expression levels of large subunit R1 (UL39) and small subunit R2 (UL40) constituting the enzyme were analyzed.

Example 2-2-1: Change in Expression Level of Large Subunit R1 (UL39)

From each of normal 5-week-old ICR mice (negative control group, N), the mouse models of herpes prepared in Example 1 (positive control group, Acy−), and the mouse models of herpes of which the lesion is applied with Acyclovir ointment for 10 days by way of the method of Example 2-1 (experimental group, Acy+), lymph node and spleen were extracted, and the total RNA was extracted from each extracted spleen, and cDNA was synthesized using the extracted total RNA. Real-time PCR was performed using the synthesized cDNA as a template and the following primers (SEQ ID NOs: 1 and 2) to comparatively analyze the expression level of large subunit R1 (UL39) (FIG. 3A).

```
UL-39_F:
                                       (SEQ ID NO: 1)
5'-GGCTGCAATCGGCCCTGAAGTA-3'

UL-39_R
                                       (SEQ ID NO: 2)
5-GGTGGTCGTAGAGGCGGTGGAA-3'
```

Figure 3A:
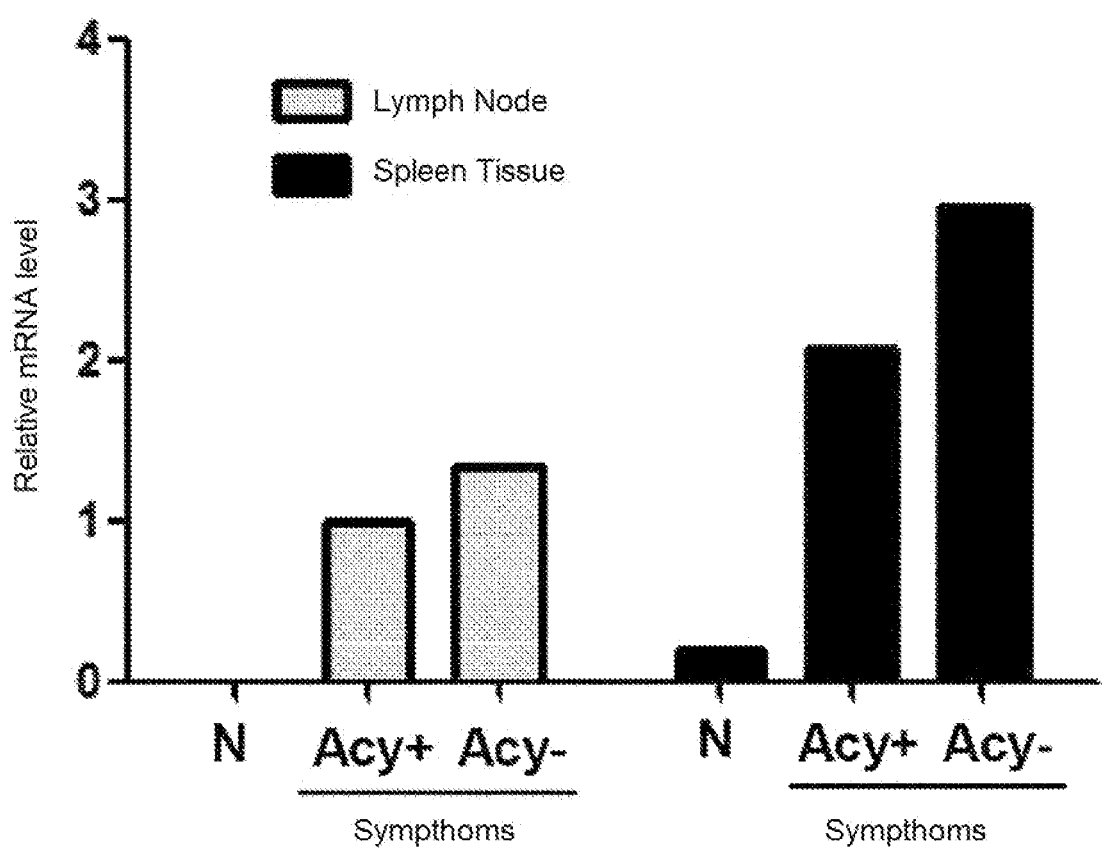
FIG. 3A is graphs illustrating the results acquired by comparing the expression levels of large subunit R1 (UL39) in HSV ribonucleotide reductase measured in the lymph node and spleen of normal 5-week-old ICR mice (negative control group, N), mouse models of herpes prepared in Example 1 (positive control group, Acy−), and mouse models of herpes of which the lesion is applied with Acyclovir ointment for 10 days by way of the method of Example 2-1 (experimental group, Acy+)

FIG. 3A is graphs illustrating the results acquired by comparing the expression levels of large subunit R1 (UL39) in HSV ribonucleotide reductase measured in the lymph node and spleen of normal 5-week-old ICR mice (negative control group, N), mouse models of herpes prepared in Example 1 (positive control group, Acy−), and mouse models of herpes of which the lesion is applied with Acyclovir ointment for 10 days by way of the method of Example 2-1 (experimental group, Acy+).

As can be seen from FIG. 3A, it has been confirmed that UL39 is not expressed or is expressed in a small amount in both the lymph node and the spleen of the negative control group (N), but the expression level of UL39 rapidly increases in the positive control group (Acy−). However, it has been confirmed that the expression level of UL39 increased in the positive control group decreases in the experimental group (Acy+).

Example 2-2-2: Change in Expression Level of Small Subunit R2 (UL40)

Figure 3B:
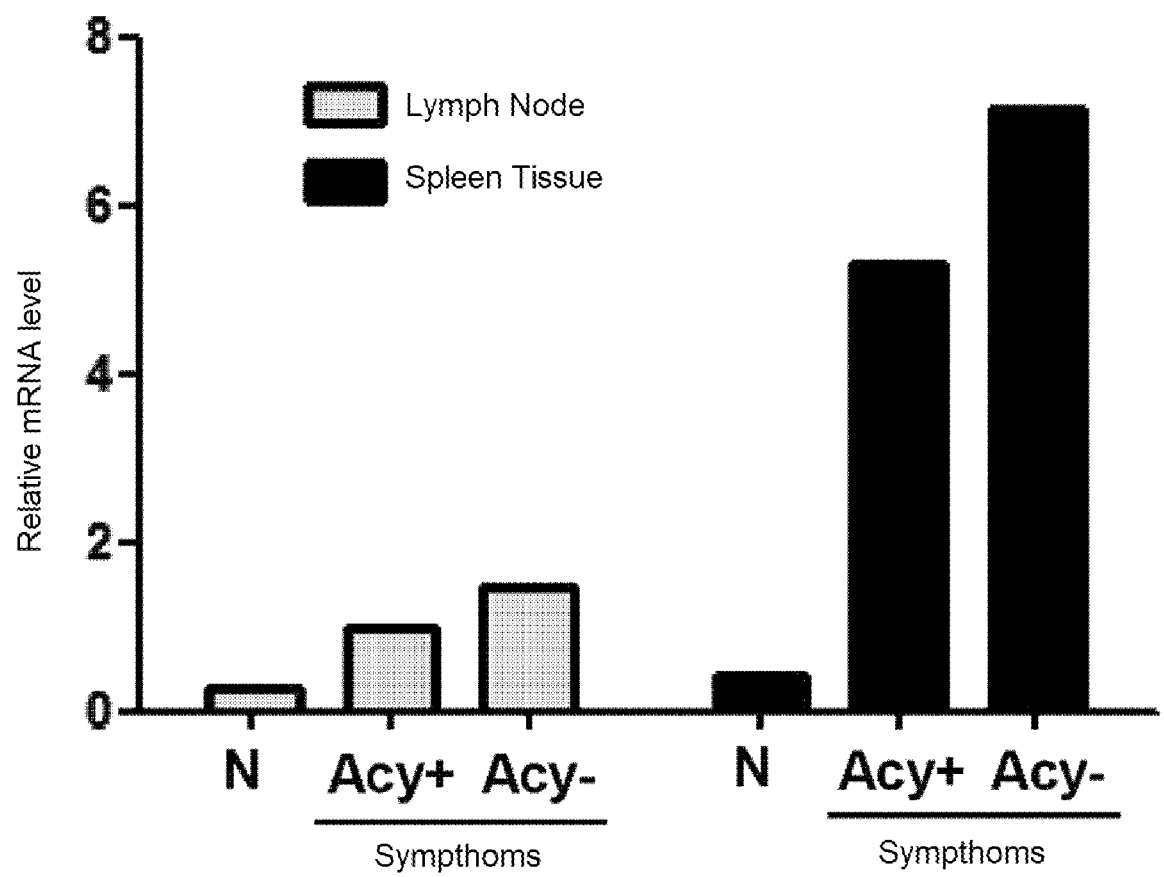
FIG. 3B is graphs illustrating the results acquired by comparing the expression levels of small subunit R2 (UL40) in HSV ribonucleotide reductase measured in the lymph node and spleen of normal 5-week-old ICR mice (negative control group, N), mouse models of herpes prepared in Example 1 (positive control group, Acy−), and mouse models of herpes of which the lesion is applied with Acyclovir ointment for 10 days by way of the method of Example 2-1 (experimental group, Acy+)

The expression level of small subunit R2 (UL40) was comparatively analyzed in the same manner as in Example 2-2-1 except that the following primers of SEQ ID NOs: 3 and 4 were used (FIG. 3B).

```
UL-40_F:
                                       (SEQ ID NO: 3)
5'-CTTCCTCTTCGCTTTCCTGTCG-3'

UL-40_R
                                       (SEQ ID NO: 4)
5'-CGCTTCCAGCCAGTCCACCTT-3'
```

FIG. 3B is graphs illustrating the results acquired by comparing the expression levels of small subunit R2 (UL40) in HSV ribonucleotide reductase measured in the lymph node and spleen of normal 5-week-old ICR mice (negative control group, N), mouse models of prepared in Example 1 (positive control group, Acy−), and mouse models of herpes of which the lesion is applied with Acyclovir ointment for 10 days by way of the method of Example 2-1 (experimental group, Acy+).

As can be seen from FIG. 3B, it has been confirmed that UL40 is expressed in a small amount in both the lymph node and the spleen of the negative control group (N), but the expression level of UL40 rapidly increases in the positive control group (Acy−). However, it has been confirmed that the expression level of UL40 increased in the positive control group decreases in the experimental group (Acy+).

Example 2-3: Analysis of Expression Level of Immunoregulatory Gene

It was expected that immune-related genes of ICR mice were activated by HSV-1 infection, and thus changes in the expression levels of these immune-related genes (T-bet, FoxP3, GATA3, and RORgt) were analyzed.

Example 2-3-1: Change in Expression Level of T-Bet Gene

Figure 4A:
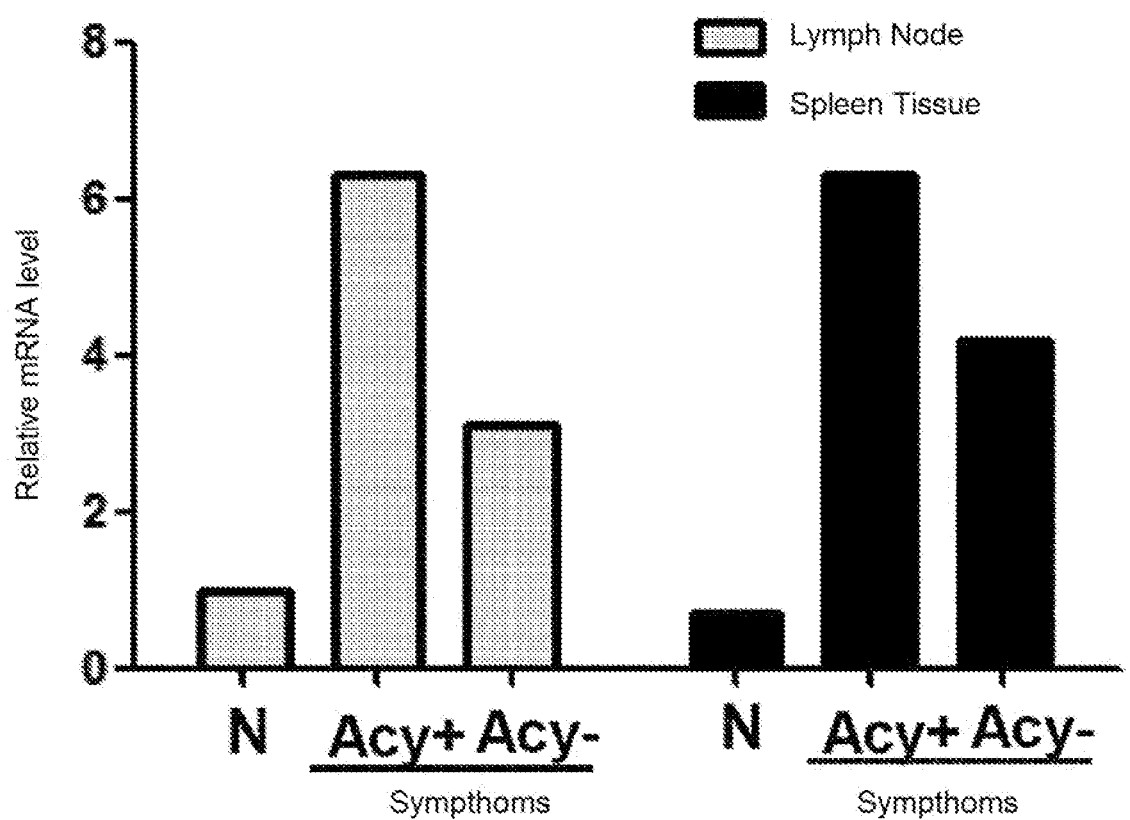
FIG. 4A is graphs illustrating the results acquired by comparing the expression levels of T-bet measured in the lymph node and spleen of normal 5-week-old ICR mice (negative control group, N), mouse models of herpes prepared in Example 1 (positive control group, Acy−), and mouse models of herpes of which the lesion is applied with Acyclovir ointment for 10 days by way of the method of Example 2-1 (experimental group, Acy+)

In order to analyze changes in the expression level of T-bet, which was a master regulator of T helper type 1 (Th1) cells, the expression level of T-bet was comparatively analyzed in the same manner as in Example 2-2-1 except that the following primers of SEQ ID NOs: 5 and 6 were used (FIG. 4A).

```
Tbet_F:
                                      (SEQ ID NO: 5)
5'-ATGTTTGTGGATGTGGTCTTGGT-3'

Tbet_R:
                                      (SEQ ID NO: 6)
5'-CGGTTCCCTGGCATGCT-3'
```

FIG. 4A is graphs illustrating the results acquired by comparing the expression levels of T-bet measured in the lymph node and spleen of normal 5-week-old ICR mice (negative control group, N), mouse models of herpes prepared in Example 1 (positive control group, Acy−), and mouse models of herpes of which the lesion is applied with Acyclovir ointment for 10 days by way of the method of Example 2-1 (experimental group, Acy+).

As can be seen from FIG. 4A, it has been confirmed that the expression level of T-bet increases in both the lymph node and the spleen in the positive control group (Acy−), in which Acyclovir ointment is not applied to mice showing symptoms of herpes after being inoculated with herpes simplex virus, as compared to that in the negative control group (Normal, N), in which normal mice are not inoculated with herpes simplex virus, and the expression level of T-bet increases in the experimental group (Acy+), in which Acyclovir ointment is administered to mice showing symptoms of herpes after being inoculated with herpes simplex virus to a higher level than in the positive control group (Acy−).

Th1 cells are known to have a role in removing the source of infection by secreting IFN-γ, and it has been analyzed that Th1 cells rapidly increase to remove the infected HSV-1 in the symptomatic positive control group (Acy−) and further increase to a higher level when Acyclovir ointment is applied so as to have a role in increasing IFN-γ secretion.

Example 2-3-2: Change in Expression Level of FoxP3 Gene

Figure 4B:
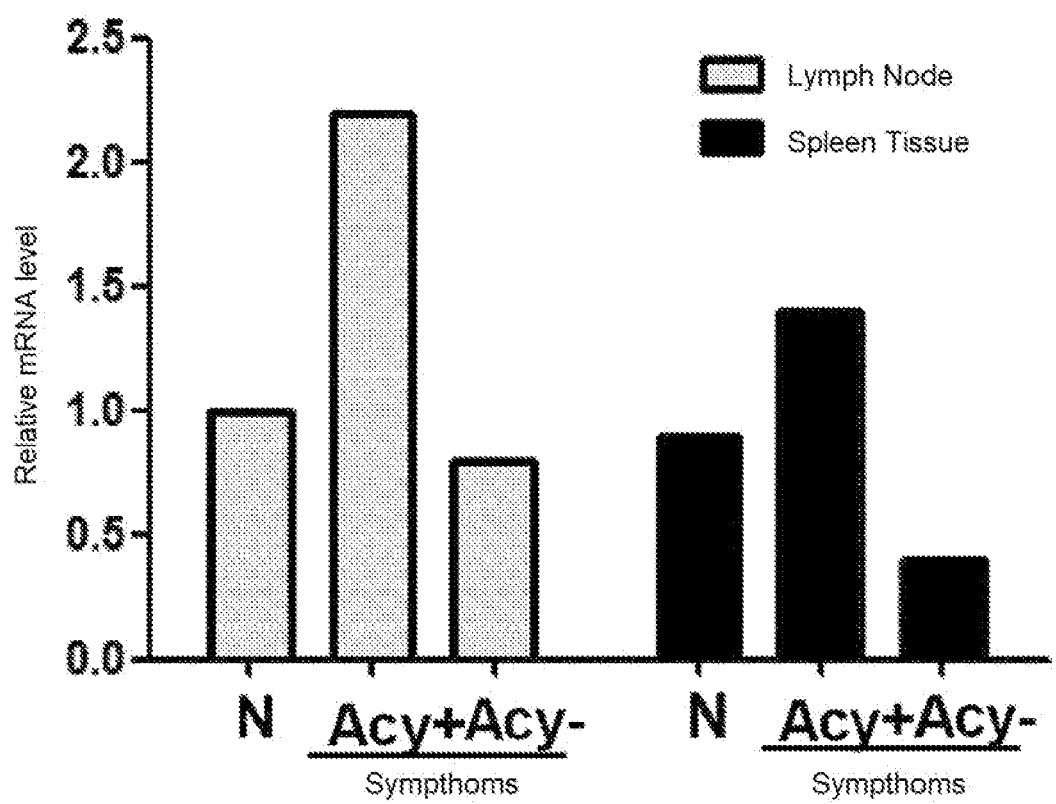
FIG. 4B is graphs illustrating the results acquired by comparing the expression levels of FoxP3 measured in the lymph node and spleen of normal 5-week-old ICR mice (negative control group, N), mouse models of herpes prepared in Example 1 (positive control group, Acy−), and mouse models of herpes of which the lesion is applied with Acyclovir ointment for 10 days by way of the method of Example 2-1 (experimental group, Acy+).

In order to analyze changes in the expression level of FoxP3, which was a master regulator of regulatory T cells (Treg), the expression level of FoxP3 was comparatively analyzed in the same manner as in Example 2-2-1 except that the following primers of SEQ ID NOs: 7 and 8 were used (FIG. 4B).

```
mFoxp3_F:
                                      (SEQ ID NO: 7)
5'-CACAATATGCGACCCCCTTTC-3' mFoxp3_R:
                                      (SEQ ID NO: 8)
5'-AACATGCGAGTAAACCAATGGTA-3'
```

FIG. 4B is graphs illustrating the results acquired by comparing the expression levels of FoxP3 measured in the lymph node and spleen of normal 5-week-old ICR mice (negative control group, N), mouse models of herpes prepared in Example 1 (positive control group, Acy−), and mouse models of herpes of which the lesion is applied with Acyclovir ointment for 10 days by way of the method of Example 2-1 (experimental group, Acy+).

As can be seen from FIG. 4B, it has been confirmed that the expression level of FoxP3 decreases in both the lymph node and the spleen in the positive control group (Acy−) as compared to that in the negative control group (N), but the expression level of FoxP3 increases in the experimental group (Acy+) to a higher level than in the negative control group (N).

From the results, it has been analyzed that the relief of inflammation by the anti-inflammatory function of regulatory T cells (Treg) may have an effect on the improvement in symptoms of herpes in the experimental group (Acy+).

Example 3: Analysis of Role of Hydrocortisone in Mouse Model of Herpes

In the preparation of mouse models of herpes prepared by way of the method of Example 1, the effect of hydrocortisone was analyzed.

Each mouse model of herpes was prepared by way of the method of Example 1 except that hydrocortisone was administered at about 50 μg/day, 150 μg/day, or 500 μg/day. Thereafter, peripheral blood was collected from each of the mouse models of herpes, peripheral blood leukocytes was isolated and obtained from the collected blood, and the frequencies of immune-related cells (CD4+, CD8+, and DX5+) contained in the peripheral blood leukocytes were measured and comparatively analyzed via flow cytometry (Tables 1 and 2). In this case, mouse models of herpes prepared without administration of hydrocortisone were used as a control group.

TABLE 1

Comparison of expression frequency of immune-related cell according to hydrocortisone dose (unit: %)

| Hydrocortisone dose (μg/day) | CD4+ | CD8+ | DX5+ |
|---|---|---|---|
| Control group | 27.4 ± 6.5 | 7.2 ± 1.2 | 5.1 ± 1.0 |
| 50 | 15.8 ± 8.8 | 6.44 ± 2.6 | 4.4 ± 2.4 |
| 150 | 12.4 ± 7.8 | 4.78 ± 1.7 | 2.89 ± 1.9 |
| 500 | 12.3 ± 4.7 | 4.2 ± 1.7 | 2.5 ± 1.9 |

As can be seen from Table 1, it has been confirmed that the frequency of immune-related cells in the blood decreases as the dose of hydrocortisone administered during the preparation of mouse models of herpes increases.

It may be considered that the synchronization rate with animals infected with HSV-1 in the natural state is higher as the level of immune-related cells in the blood is lower in the mouse models of herpes.

From the results, it has been analyzed that the dose of hydrocortisone may be a major factor involved in the synchronization rate of the model with the actual infected animal in the preparation of mouse models of herpes provided in the present invention.

Hence, in order to verify the analysis results, the prevalence rate of herpes was compared for the mice of the control group administered with HSV-1 singly and the mice of the experimental group administered with HSV-1 and hydrocortisone at 150 μg/day in combination (Table 2).

TABLE 2

Comparison of prevalence rate of herpes (symptomatic mice/total mice) in mice administered with HSV singly and mice administered with HSV + hydrocortisone in combination (unit: %)

| | Prevalence rate |
|---|---|
| Administered with HSV singly | 5.8% (3/45) |
| Administered with HSV + hydrocortisone in combination | 14.7% (14/95) |

As can be seen from Table 2, it has been confirmed the prevalence rate of herpes in the mice administered with HSV-1 and hydrocortisone in combination is about 2.5 times the prevalence rate of herpes in the mice administered with HSV-1 singly.

Hence, it has been found that the dose of hydrocortisone is a major factor affecting the improvement in the synchronization rate of a mouse model that simulates the symptoms of herpes in an actual infected animal in the preparation of mouse models of herpes provided in the present invention, and a mouse model of herpes can be more efficiently prepared by administering hydrocortisone.

Meanwhile, from only the results of Tables 1 and 2, it has been found that it is preferable to administer hydrocortisone as much as possible, and it is experimentally preferable to administer hydrocortisone at 150 μg/day to 500 μg/day in order to prepare a mouse model of herpes having a high synchronization rate with animals infected with HSV-1 in the natural state.

However, since hydrocortisone is a steroidal hormonal agent, it is expected that there is a possibility of causing various side effects when hydrocortisone is administered to mice in an excessive amount, these side effects cause symptoms other than HSV-1 infection, and there is a possibility of distorting the experimental results using mouse models of herpes.

Hence, it has been analyzed that the appropriate dose of hydrocortisone administered during the preparation of the mouse model of herpes of the present invention is 150 μg/day to 200 μg/day per average body weight of mice (25 g).

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the present invention is defined by the appended claims rather than by the description preceding them, and therefore all changes and modifications that fall within metes and bounds of the claims or equivalents of such metes and bounds are therefore intended to be embraced by the claims.

The invention claimed is:

1. A method of preparing a mouse model of herpes, the method comprising:

(a) damaging a site of surface of a mouse, inoculating the damaged site with herpes simplex virus type 1 (HSV-1), and then rearing the mouse; and (b) injecting the reared mouse with hydrocortisone, wherein the injection of hydrocortisone to the mouse is performed every day for 3 to 10 consecutive days from the day after the inoculation with herpes simplex virus type 1 has been completed, and wherein an amount of hydrocortisone injected is 75 μg/day to 300 μg/day per average body weight of mice, said average body weight being 25 g.

2. The method of preparing a mouse model of herpes according to claim 1, wherein the site to be inoculated with HSV-1 is a skin region of a mouse.

3. The method of preparing a mouse model of herpes according to claim 1, wherein an amount of HSV-1 inoculated is $1 \times 10^3$ pfu to $1 \times 10^5$ pfu.

4. The method of preparing a mouse model of herpes according to claim 1, wherein the injection of hydrocortisone is performed via an intramuscular injection, an intraperitoneal injection, or a vascular injection.

5. The method of preparing a mouse model of herpes according to claim 1, wherein the amount of hydrocortisone injected is 150 μg/day to 200 μg/day per average body weight of mice.

\* \* \* \* \*

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
ggctgcaatc ggccctgaag ta                                           22

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
ggtggtcgta gaggcggtgg aa                                           22

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
```

```
cttcctcttc gctttcctgt cg                                            22

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
cgcttccagc cagtccacct t                                             21

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
atgtttgtgg atgtggtctt ggt                                           23

<210> SEQ ID NO 6
<211> LENGTH: 17
<212> TYPE: DNA
<213> ORGANISM: Artificial Sequence
<220> FEATURE:
<223> OTHER INFORMATION: primer

<400> SEQUENCE: 6
cggttccctg gcatgct                                                  17

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
cacaatatgc gacccccttt c                                             21

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
aacatgcgag taaaccaatg gta                                           23
```